(12) United States Patent
Al-Thallab et al.

(10) Patent No.: US 8,128,876 B2
(45) Date of Patent: Mar. 6, 2012

(54) APPARATUS FOR PROVIDING POLLUTION FREE AIR

(76) Inventors: Fatema S. Al-Thallab, Aljahra (KW); Omar Al-Bannai, Alrumaithiyah (KW); Ahmad Al Hashash, Alrabia (KW)

( * ) Notice: Subject to any disclaimer, the term of this patent is extended or adjusted under 35 U.S.C. 154(b) by 325 days.

(21) Appl. No.: 12/401,683

(22) Filed: Mar. 11, 2009

(65) Prior Publication Data
US 2010/0233019 A1    Sep. 16, 2010

(51) Int. Cl.
*A61L 9/00* (2006.01)
(52) U.S. Cl. ............ 422/120; 422/4; 422/124; 454/156; 454/158; 454/159
(58) Field of Classification Search .............. 422/4, 120, 422/121, 124; 454/156, 158, 159
See application file for complete search history.

(56) References Cited

U.S. PATENT DOCUMENTS

| | | | |
|---|---|---|---|
| 3,878,570 A | 4/1975 | Donnelly | |
| 4,508,115 A | 4/1985 | Warncke | |
| 5,943,716 A | 8/1999 | Chu | |
| 6,068,322 A | 5/2000 | Kuester | |
| 7,481,234 B1 * | 1/2009 | Gustafson et al. | 135/91 |

* cited by examiner

*Primary Examiner* — Sean E Conley
(74) *Attorney, Agent, or Firm* — Lowe Hauptman Ham & Berner, LLP

(57) ABSTRACT

An apparatus for providing pollution free air to an individual includes an enclosed or semi-enclosed space or compartment for surround or partially surrounding an individual's head or upper body to separate the individual from polluted air. A filter assembly and fan forcing polluted air through the filter assembly and into the enclosure. The filter assembly includes a first filter for removing relatively large particles such as sand or dust from the polluted air while a second HAPA filter removes airborne allergens before forcing non-polluted air into the enclosed or semi-enclosed space.

1 Claim, 6 Drawing Sheets

APPARATUS FOR PROVIDING POLLUTION FREE AIR

FIELD OF THE INVENTION

This invention relates to an apparatus and method for providing pollution free air to a child or older individual and more particularly to an apparatus and methods for reducing health risks related to particulate matter.

BACKGROUND FOR THE INVENTION

Particulate matter (PM) has been linked to a range of serious respiratory and cardiovascular health problems. It has also been recognized that such problems are particularly serious for small children and infants. For example in Kuwait, other Middle Eastern countries and desert regions sand or dust entrained in the air is a constant problem.

According to the National Center for Environmental Research with an Office in Washington, D.C., the key effects associated with exposure to ambient particulate matter include: premature mortality, aggravation of respiratory and cardiovascular disease, as indicated by increased hospital stays, emergency room visits, school absences, work days lost and restricted activity days, aggravated asthma, acute respiratory symptoms, chronic bronchitis, decreased lung function and increased risks of myocardial infarction. As reported, recent epidemiologic studies estimate that exposure to particulate matter may result in tens of thousands of excess deaths per year and many more cases of illnesses among the U.S. population.

Numerous attempts to protect individuals from the harmful effects of airborne particulate matter, for example a U.S. States Patent of Chu, U.S. Pat. No. 5,943,716 discloses an air conditioned bed hood for a baby. As disclosed therein, an air-conditioned bed hood for a baby is connected with an air cleaner having a heater and humidifier for inputting clean air of constant temperature and moisture. In this matter, a live baby is provided with a comfortable environment and avoids diseases caused by smoke, dust or pollen. Moreover, when the power is shut down, the air pressure seal of the bed hood is automatically released so that the baby will not be asphyxiated due to a lack of air.

A more recent patent of Kuster, U.S. Pat. No. 6,068,322 discloses a transparent canopy for covering a seated child in a baby-buggy for protecting the child from exposure to ambient-air pollution. As disclosed, a powered filter unit blows filtered ambient air into the top of the compartment between the canopy and the seat. The bottom of the compartment is open where a lower apron portion of the canopy hangs spaced from the child's legs. Entry of polluted air via the bottom opening is blocked by operating a powered filter unit to create positive pressure within the compartment. In this way, filtered air flows downwardly across the child's face and upper body. A meshed insert in the canopy gives balanced ventilation and prevents heat build up.

A more secure protective bed unit is disclosed in a U.S. patent of Walling, U.S. Pat. No. 7,137,881. As disclosed, a protective bed includes a shield of bullet-proof and impact resistant material that surrounds a metal frame. The shield operably separates to provide access to an interior sleeping area. Quick access doors are located on either side of the bed and a ventilator system provides for climate control as well as filtering harmful substances from the air. A re-breather scrubs carbon-dioxide from the air within the unit to allow a user to close the unit to outside air.

It is Applicant's belief that none of the above-identified patents or other prior art fully address the serious problem of particulate matter entrained in the air where an individual lives, plays and works in an environment of relatively high loading of sand, dust and other particulate matter entrained in ambient air. None of the aforementioned patents fully addresses the problem of infants and young children with respiratory problems such as asthma and bronchitis.

Accordingly, it is presently believed that there is a need and a potential commercial market for an apparatus in accordance with the present invention. There should be a need because such apparatus will reduce the problem related to particulate matter in the environment and one that is particularly applicable for babies and small children and at the same time addresses the issues of cost vs. removal of particulate matter. For example, such apparatus can be designed to remove essentially all particulate matter for small children suffering from asthma or other respiratory diseases. It is also believed that the apparatus in accordance with several embodiments of the invention are durable and reliable while others that may be fragile are more appropriate for those with less serious problems and/or a need to work or play in a polluted environment.

BRIEF SUMMARY OF THE INVENTION

In essence, the present invention relates to an apparatus and method for providing pollution free air to an individual or in a preferred embodiment to a baby or small child with respiratory problems. The apparatus comprises an enclosed or semi-enclosed space surrounding or partially surrounding an individual to separate the individual's mouth and nose from a polluted environment. A filter assembly and a fan for drawing air through the filter assembly and into the enclosed or semi-enclosed space and for creating turbulence within the enclosure or semi-enclosed space are provided. The filter assembly includes a first filter for removing sand and other particles having a particle size of about 75 to 100 microns or greater and a second high efficiency particulate air filter for removing air borne allergens and other particles having particle size of about 10 microns to about 75 microns before directing filtered air into an enclosed or semi-enclosed space, and means for exhausting spent air from the enclosed or semi-enclosed space.

A preferred embodiment of the invention includes a third filter and a source of high intensity ultraviolet U.V. light. In the preferred embodiment of the invention the first filter removes particles having a size of about 75 microns or greater. The second filter removes particles having a size of about 10 to 75 microns and the third filter removes particles of about 2.5 microns to about 10 microns. This embodiment of the invention may also include means for energizing the high intensity U.V light to kill any live allergens remaining in the filtered air.

The invention will now be described in connection with the following drawings wherein like reference numerals have been used to identify like parts.

DESCRIPTION OF THE PREFERRED EMBODIMENTS OF THE INVENTION

It has been estimated that air pollution kills about 50,000 people yearly. It has also been recognized that air pollution contributes to respiratory problems including chest infection, bronchial asthma, cough, pertossis (whooping cough) and/or infection due to Bortella Parapertussis, common colds and upper respiratory track infection. Such pollution has also been associated with allergies of the eyes, nose and chest.

As reported by the American Lung Association, the health effects of particulate matter, short term increases in particle pollution have been linked to deaths from respiratory and cardiovascular causes including strokes, increased number of heart attacks especially among the elderly, inflammation of lung tissue in young healthy adults, increased hospitalization for cardiovascular disease including strokes, increased emergency room visits from patients suffering from acute respiratory ailments, increased hospitalization for asthma among children and increased severity of asthma attacks in children. Further, the American Lund Association reports that year round exposure to particle pollution has also been linked to: increased hospitalization for asthma attacks for children living within 200 yards of roads with heavy truck or trailer traffic, slowed lung function growth in children and teenagers, sufficient damage to the small airways of the lungs, increased risk of dying from lung cancer and increased risk of death from cardio vascular disease.

Other biological factors that cause allergies and other problems are humidity which contributes to the growth of molds and fungi, and other natural substances which spread in the air like plant spores. The problem of internal air pollution is also a serious concern. Some of the most important sources of internal pollution are cigarettes and other burnt products like nitro oxides, carbon monoxide and carbon dioxide as well as other microbial substances which pollute the air as for example molds, viruses, bacteria and spores.

In desert areas, especially in Kuwait and nearby countries, dust in the air which comes from the desert is in itself hazardous without any interaction with other substances. However, in desert areas near oil production facilities particularly near oil fires such as those in Kuwait following the Iraqi occupation, the sand or dust may include oil and other poisonous substances that may be inhaled into the human lungs.

At times, it is important or even necessary for children, the elderly or others to leave a home or hospital, school or other structure when the atmosphere is heavily polluted with dust and/or other contaminants. In such times it is desirable to provide a portable unit to minimize or at least reduce the effects of particulate pollution on an individual with asthma or other respiratory malady from naturally occurring dust and other pollutants.

Figure 1:
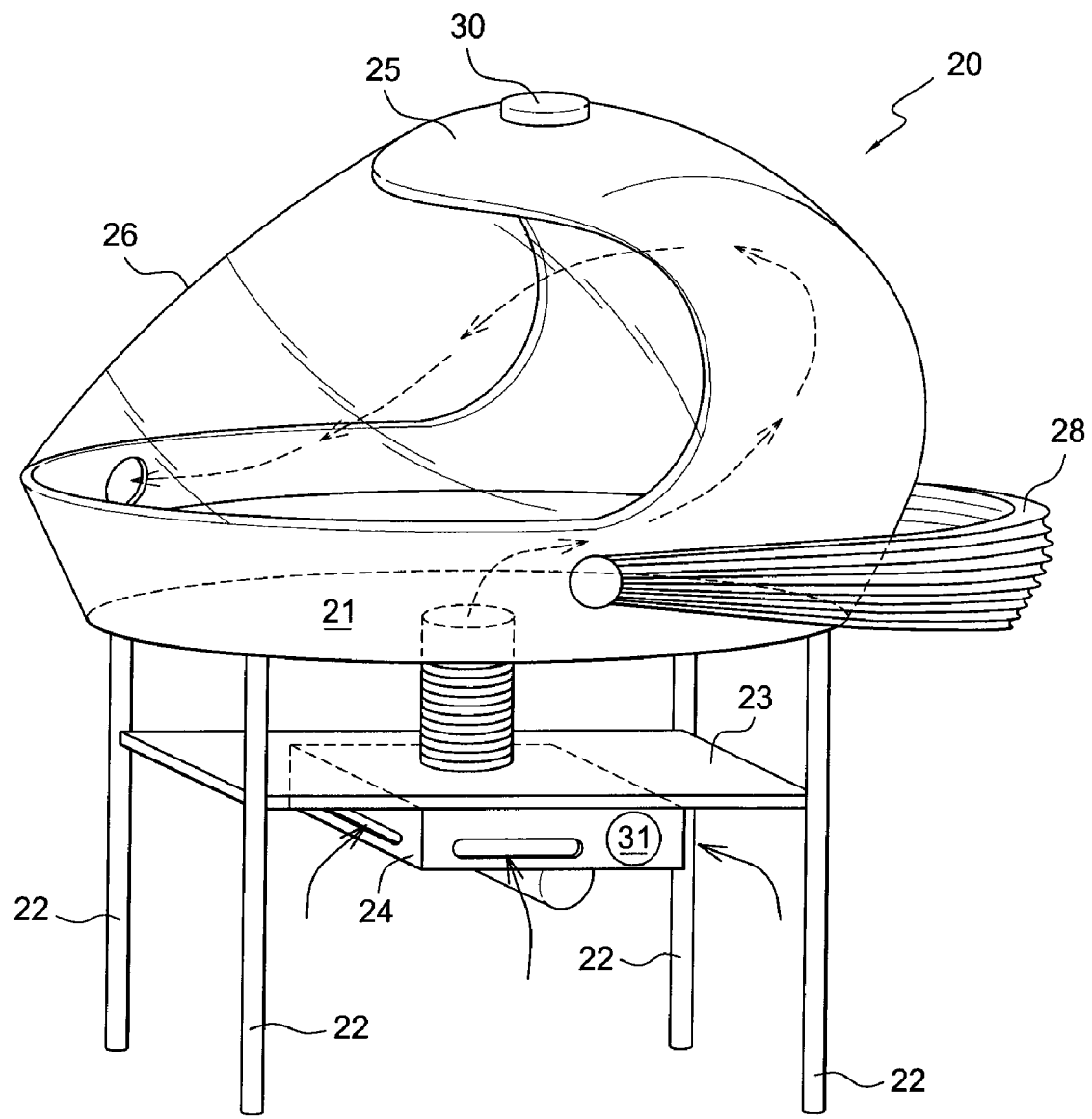
FIG. 1 is a schematic illustration of a child's crib in accordance with the invention with a fire screen or cover in a retracted position.
Figure 2:
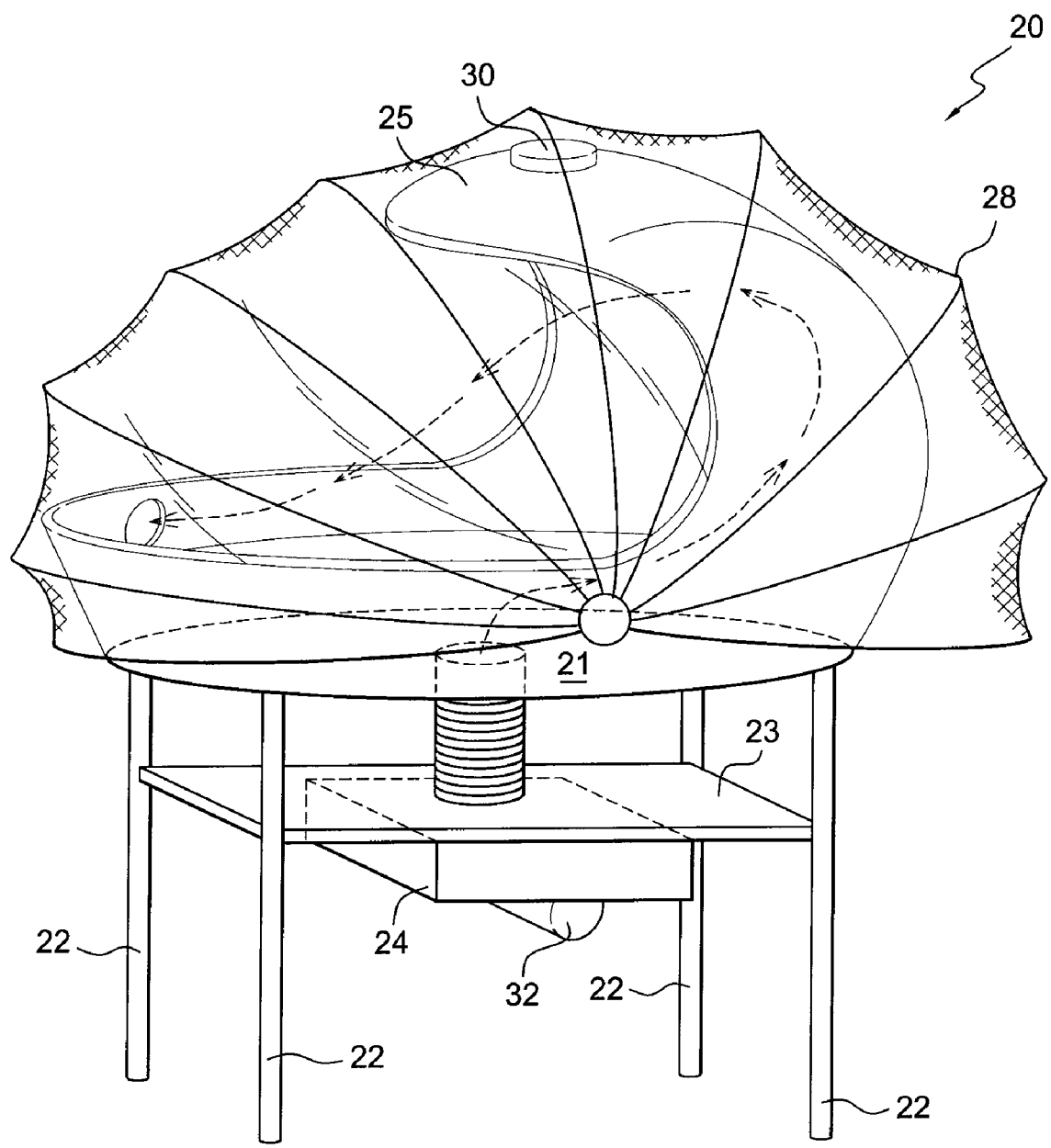
FIG. 2 is a schematic illustration of the child's crib shown in FIG. 1 but with the fire screen in an open position.

As shown in FIGS. 1 and 2 a baby's bed or crib 20 is equipped with a foldable cover 28 and a filter assembly 24. The crib 20 also includes a hood 25 and transparent cover 26.

The transparent cover 26 may be replaced by the foldable cover 28 when the foldable cover 28 is used to cover the crib 20 as shown in FIG. 2. In that case the foldable cover 28 will be made of a transparent plastic material.

The crib 20 also includes a bottom member or base 21 for supporting a mattress and child (not shown) and upwardly extending side walls surrounding the base 21. The foldable cover 28 is attached to the upwardly extending sides and rotates between an open position shown in FIG. 1 and a cover position shown in FIG. 2.

Four legs 22 support the base 21 at a suitable height above the floor. The four legs 22 and an intermediate shelf 23 are of conventional design. However, in this embodiment of the invention, the shelf 23 supports the filter assembly 24. The filter assembly 24 is operatively connected to the interior of the crib by means of a flexible hose or the like. The flexible hose may be connected to deliver filtered air through the base 21 or sides of the crib or through an alternate inlet 30 in the hood 25 as long as care is taken so that the baby's body can not close off the source of filtered air.

An air inlet 31 or plurality of slots may be used for driving the air into the filter assembly 2. In addition, a heater/humidifier 32 may be provided to maintain the filtered air at a preselected temperature and humidity.

Figure 2B:
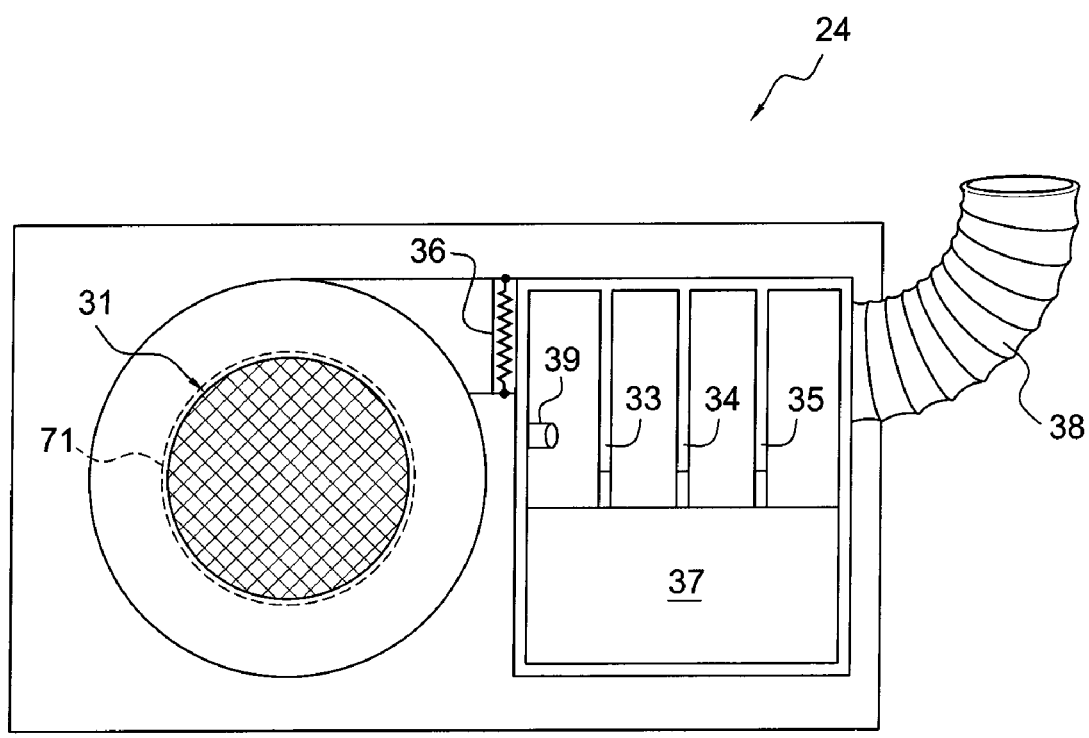
FIG. 2b is a schematic illustration of a filter assembly as used in the present invention.

A filter assembly 24 in accordance with a preferred embodiment of the invention is shown in FIG. 2B. The filter assembly 24 includes a centrifugal blower 71 disposed behind the inlet 31 for driving ambient air into the filter assembly 24 and forcing the air across a heater 36. The heater 36 is coupled with a temperature sensor/control (not shown) so that filtered air delivered to the flexible hose 38 is maintained at a preselected temperature. The heated air is forced through a first filter 33 for removing the course particles as for example inhalable particles that is greater than 10 microns but smaller than 100 microns, a second filter 34 for removing thoracic dust i.e. less than 10 microns and a third filter 35 for removing respiratory sand and airborne allergens i.e. less than 5 microns. The filter assembly 24 also includes a water tank 37 and/or sponge for adding humidity to the air and a tube 39 for adding water to the tank 37. Suitable means for measuring the humidity of the air supplied to hose 38 may also be utilized.

Figure 3:
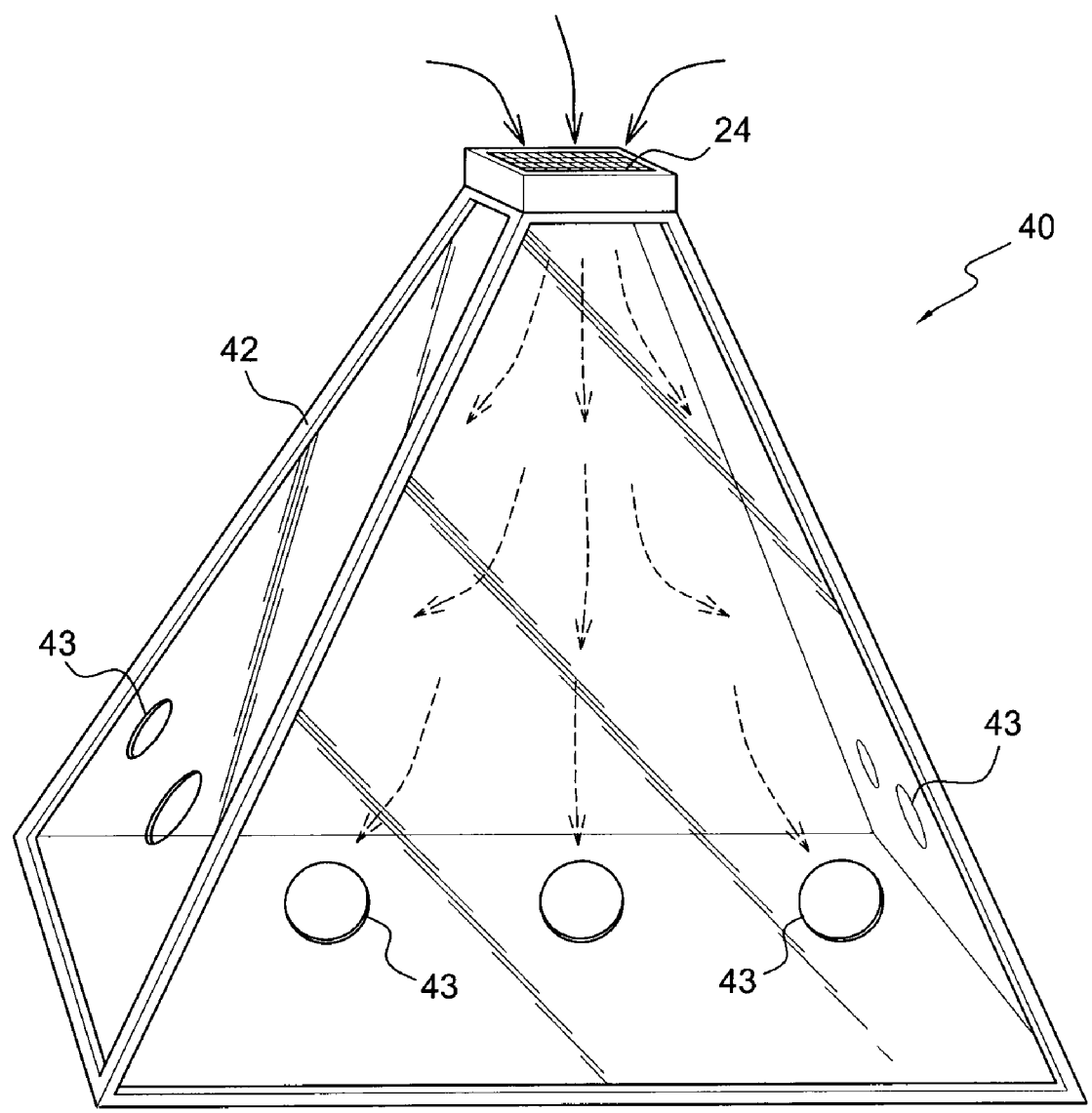
FIG. 3 is a schematic illustration of a further embodiment of the invention.

FIG. 3 illustrates another embodiment of the invention that provides a tent like structure 40 for covering a child's playpen (not shown) or the like. The structure 40 is in the shape a frustum of a pyramid and includes structural members 42 with a filter assembly 24 at the top of the structure and a plurality of openings 43 in a lower portion thereof for exhausting spent air.

Figure 4:
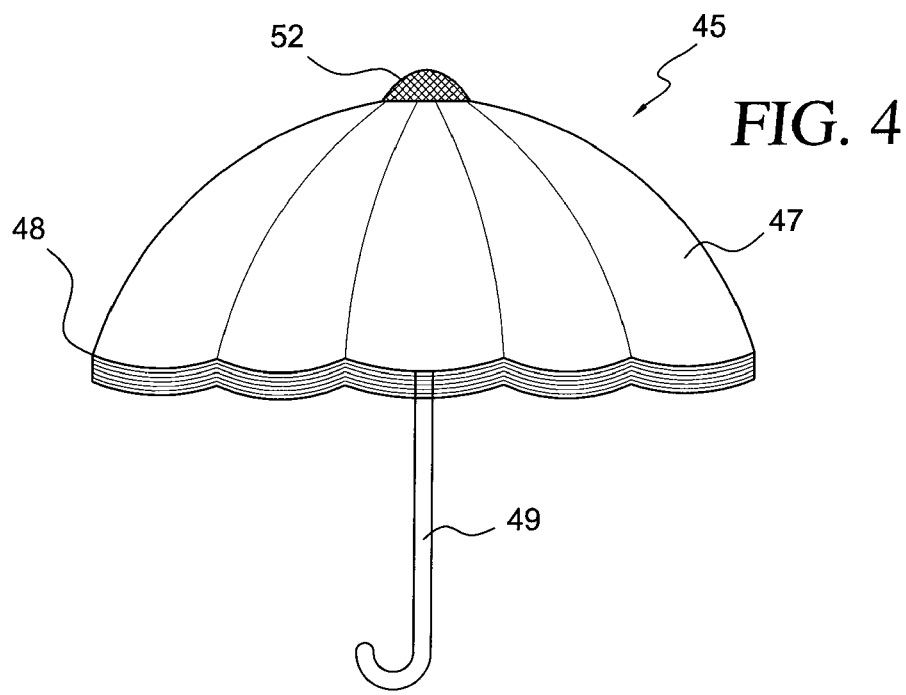
FIG. 4 is a schematic illustration of a another embodiment of the invention with a folded pollution curtain.
Figure 5:
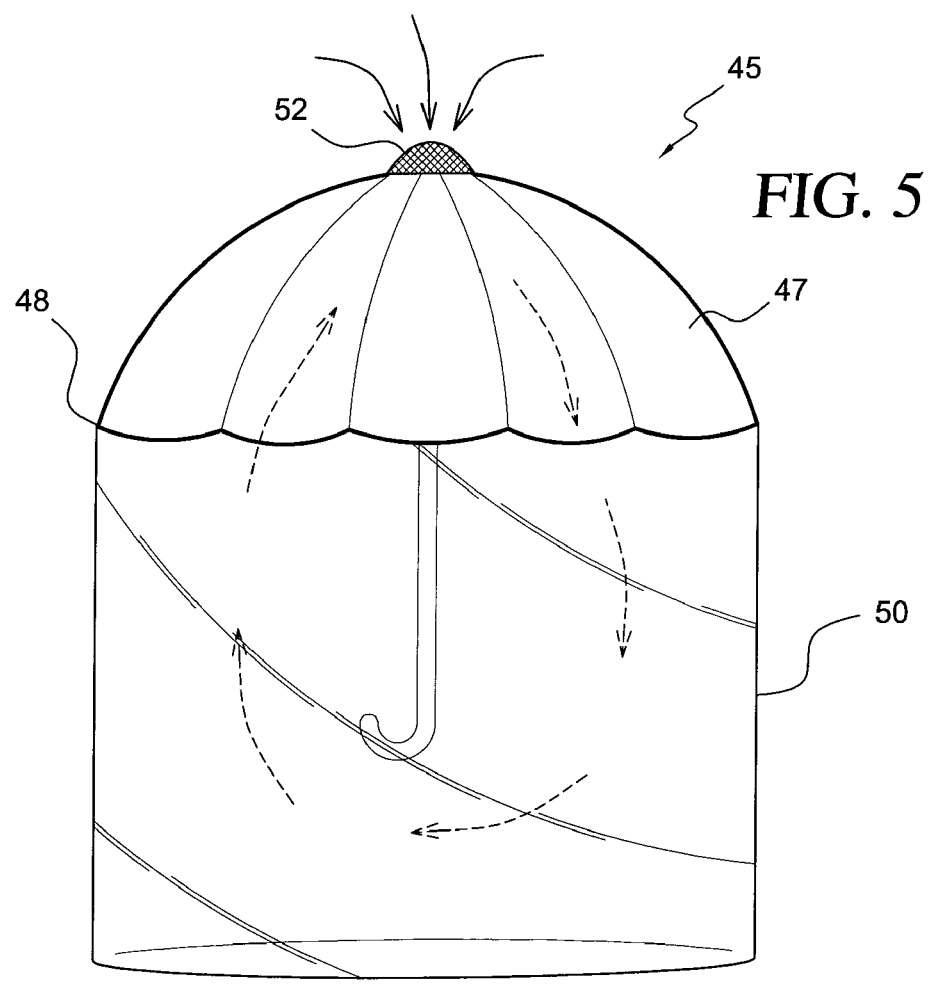
FIG. 5 is a schematic illustration of the embodiment of the invention as shown in FIG. 4 but with the pollution curtain unfolded.

As shown in FIGS. 4 and 5, a portable unit 45 in the form of an umbrella 48 provides needed protection. The umbrella 48 includes an upper portions 47, an outer periphery 48 and a handle 49. The portable unit 45 is in the form of an umbrella 48 and provides needed protection for the short term exposure to relatively high concentrations of particulate matter. The umbrella 48 includes an upper cover or canopy 47 having an outer periphery 48 and a post including a handle 49. The basic structure of the umbrella is conventional with a plurality of main ribs and stretchers (not shown) as well as a mechanism for opening and closing the umbrella. For example, the basic umbrella may be similar to the one shown in U.S. Pat. No. 7,210,491 which is incorporated herein in its entirety by reference.

In this embodiment of the invention the umbrella includes a transparent curtain 50 that is attached to the outer periphery of the canopy and hangs down over the head and shoulders of an individual. A filter assembly 52 includes a fan for directing a flow of air is mounted in the central part of the umbrella at the top of the post or pole. In this embodiment of the invention only two filters are contemplated. A first filter screens out materials larger than about 65 micronomiters and a second filter that takes out smaller particles as for example 10 to 25 microns.

Figure 6:
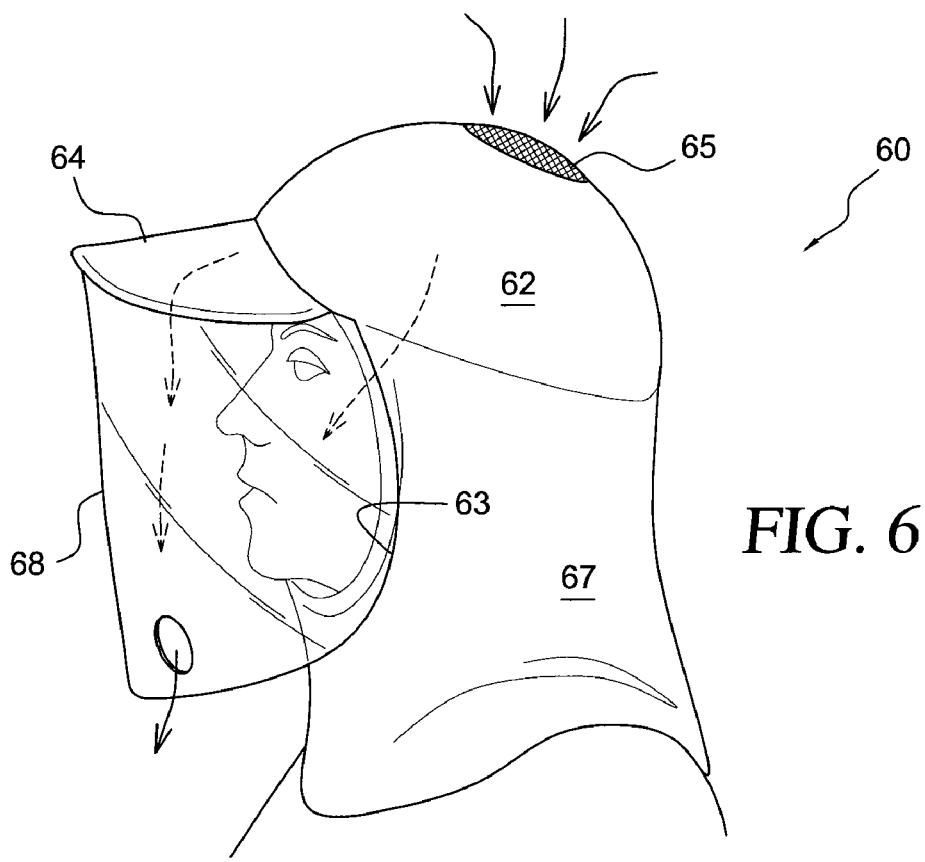
FIG. 6 is a schematic side view of a still further embodiment of the invention.
Figure 7:
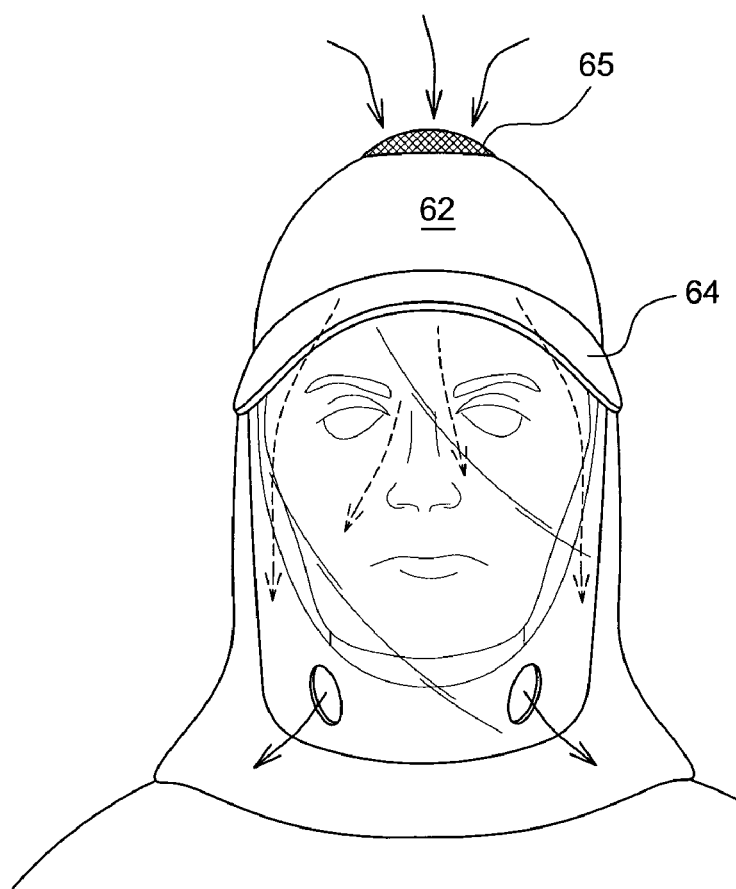
FIG. 7 is a schematic front view of the embodiment of the invention shown in FIG. 6.

FIGS. 6 and 7 illustrate a further embodiment of the invention wherein the apparatus for providing pollution free air comprises a hat or cap 60. The hat or cap 60 resembles a helmet or balaclava and includes a crown 62, visor 64 with a filter assembly 65 disposed in an upper portion of the crown 62. As illustrated, the crown 62 wraps around the head with a lower portion 67 encircling an individual's neck but leaving an open area 63 in front of an individual's face in the form of a balaclava. However in the present case the visor 64 extends outwardly from the upper portion of the opening 63 with a transparent face shield 68 extending downwardly therefrom and fitting tightly around the sides of the opening 63. In this way the face shield 68 that may be in the form of a flexible plastic sheet forms a semi-enclosed compartment with an opening in a bottom portion thereof.

The filter assembly 65 includes a fan, pair of filters and ducting to duct a flow of filtered air across the individual's face.

While the invention has been described in connection with its accompanying drawings it should be recognized that changes and modifications may be made therein without departing from the scope of the appended claims.

What is claimed is:

1. An apparatus for providing pollution free air to an individual comprising:

a semi-enclosed space particularly surrounding an individual to separate the individual's mouth and nose from a polluted environment;

wherein said semi-enclosed space is in the form of an umbrella having an upper canopy, a post including a handle, a plurality of ribs supporting said canopy and a mechanism for opening and closing said umbrella and a transparent curtain hanging down from said outer periphery to cover an upper torso of an individual and wherein a central part of the upper part of the umbrella defines an opening to draw air in from the atmosphere; and, a filter assembly and a fan disposed in said upper central portion of said umbrella for drawing air through said filter assembly and into said semi-enclosed space and for creating turbulence within said semi-enclosed space and wherein said filter assembly includes a first filter for removing sand or dust particles having a size of about 65 microns or greater from the air drawn into and through said first filter, and a second high efficiency particulate air filter spaced from said first filter for removing airborne allergens having particle sizes of about 10 microns to about 65 microns from said air before directing filtered air into said semi-enclosed space; and, wherein said filter assembly includes a heater for heating air to a preselected temperature, a water tank and a sponge for adding humidity to the air and means for measuring the humidity of the air supplied to said semi-enclosed space and said filter assembly further including a high intensity source of ultra-violet light and means for energizing said ultra-violet light to kill any live bacteria and virus; and, wherein said fan creates a positive pressure within said semi-enclosed space and exhausts spent air from said semi-enclosed space.

\* \* \* \* \*